US009318798B2

(12) United States Patent
Crivelli et al.

(10) Patent No.: US 9,318,798 B2
(45) Date of Patent: Apr. 19, 2016

(54) ANTENNA INSULATION FOR AN IMPLANTABLE MEDICAL DEVICE

(75) Inventors: Rocco Crivelli, Bellinzona (CH); Thierry Pipoz, Le Locle (CH)

(73) Assignee: CODMAN NEURO SCIENCES SARL (CH)

( * ) Notice: Subject to any disclaimer, the term of this patent is extended or adjusted under 35 U.S.C. 154(b) by 1391 days.

(21) Appl. No.: 12/254,192

(22) Filed: Oct. 20, 2008

(65) Prior Publication Data

US 2010/0100156 A1 Apr. 22, 2010

(51) Int. Cl.
| H01Q 1/30 | (2006.01) |
| A61N 1/372 | (2006.01) |
| H01Q 1/27 | (2006.01) |
| H01Q 1/36 | (2006.01) |
| A61N 1/375 | (2006.01) |
| H01Q 1/40 | (2006.01) |
| H01Q 11/08 | (2006.01) |

(52) U.S. Cl.
CPC .............. *H01Q 1/30* (2013.01); *A61N 1/37229* (2013.01); *H01Q 1/273* (2013.01); *H01Q 1/362* (2013.01); *H01Q 1/40* (2013.01); *H01Q 11/08* (2013.01); *A61N 1/3754* (2013.01)

(58) Field of Classification Search
CPC ........... H01Q 1/30; H01Q 1/273; H01Q 1/40; H01Q 11/08; H01Q 1/362; A61N 1/37229; A61N 1/3754
USPC .......................................... 607/32, 36–37, 60
See application file for complete search history.

(56) References Cited

U.S. PATENT DOCUMENTS

| 5,301,687 | A | * | 4/1994 | Wong et al. ..................... 607/116 |
| 6,009,350 | A | * | 12/1999 | Renken ............................ 607/32 |
| 6,456,256 | B1 | | 9/2002 | Amundson et al. |
| 7,047,076 | B1 | | 5/2006 | Li |
| 7,231,252 | B2 | * | 6/2007 | Duncan et al. ................... 607/36 |
| 2001/0016702 | A1 | * | 8/2001 | Benjamin ........................ 604/19 |
| 2001/0016761 | A1 | * | 8/2001 | Rudie et al. .................... 607/101 |
| 2005/0203584 | A1 | | 9/2005 | Twetan |
| 2006/0020300 | A1 | | 1/2006 | Nghiem |
| 2006/0247712 | A1 | | 11/2006 | Fuller |
| 2007/0128940 | A1 | * | 6/2007 | Ho et al. ................... 439/620.05 |
| 2008/0135217 | A1 | * | 6/2008 | Turovskiy et al. ........ 165/104.33 |
| 2008/0228270 | A1 | * | 9/2008 | Dahlberg .................... 623/11.11 |
| 2010/0082080 | A1 | * | 4/2010 | Mateychuk ..................... 607/60 |

FOREIGN PATENT DOCUMENTS

| JP | 2006297079 | 11/2006 |
| WO | WO 2005115540 | 12/2005 |

OTHER PUBLICATIONS

European Search Report 09252446.1 dated Feb. 11, 2010.

* cited by examiner

*Primary Examiner* — Catherine Voorhees

(57) ABSTRACT

An implantable medical device includes a hermetically sealed housing that contains electronic circuitry. A feedthrough is disposed on an external surface of the housing. An antenna wire is disposed around the external surface of the housing. The antenna wire has one end connected to the feedthrough so that the antenna wire is in electric communication with at least a portion of the electronic circuitry. A heat shrink tube is sealingly disposed about substantially the entire external surface of the antenna wire to prevent fluids from contacting the antenna wire and thereby detuning the antenna wire. An antenna surround is disposed about the tube.

16 Claims, 2 Drawing Sheets

FIG. 1
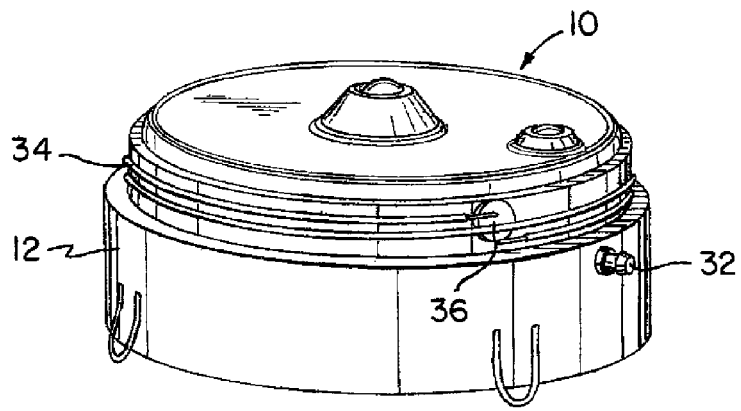
FIG. 2
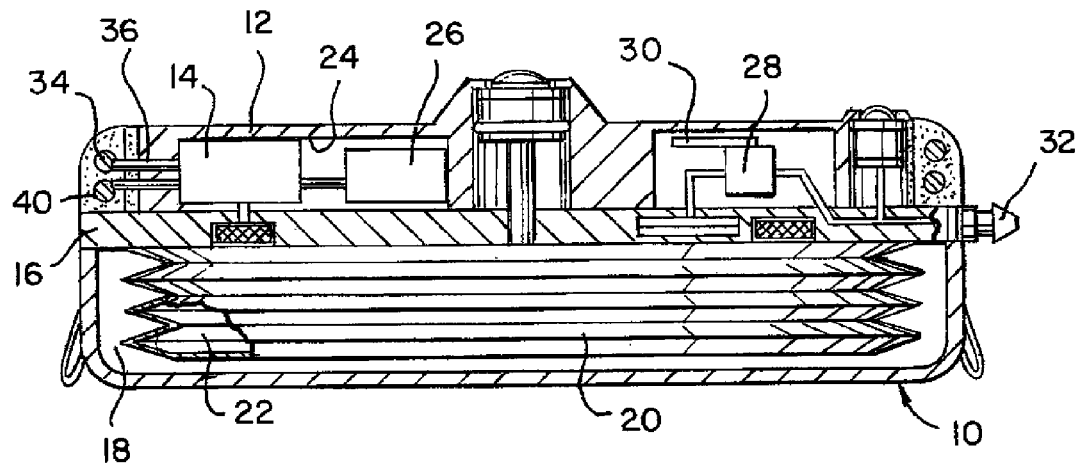
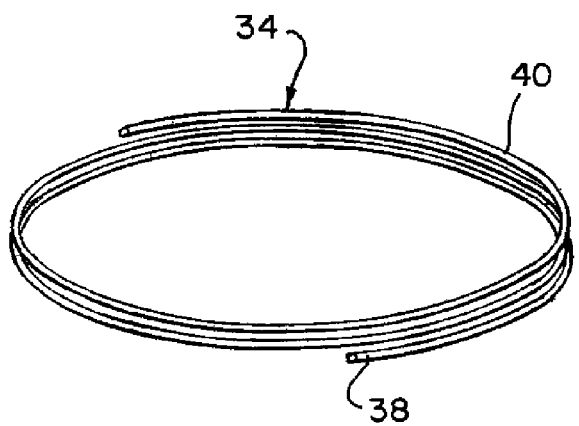
FIG. 3

ANTENNA INSULATION FOR AN IMPLANTABLE MEDICAL DEVICE

BACKGROUND OF THE INVENTION

1. Field of the Invention

The present invention relates to an antenna for use in an implantable medical device. More specifically, the present invention relates to an antenna insulation for an external antenna of an implantable medical device.

2. Discussion of Related Art

Some implantable medical devices communicate with an external device via radio frequency (RF) telemetry. To achieve this, the implantable medical device requires an antenna to communicate with the external device.

U.S. Pat. No. 6,456,256 disclosed placing the antenna on the exterior of the implant housing to permit far-field radiation. The antenna is disclosed as being embedded in an antenna compartment that is made of dielectric material. The antenna is disclosed as not being welded to a feedthrough, but simply is routed from the transmitting and receiving electronic circuitry within the housing through the feedthrough to the dielectric compartment with no connections.

An external control unit has a radio frequency emitter that can emit a carrier frequency f. When manufacturing the implantable medical device and external control unit associated therewith, both the external control unit antenna and the antenna of the implantable medical device are tuned at a carrier frequency f. However, once in use, any contact of bodily fluid with the antenna wire of the implantable device will generate stray electrical capacitances and detune the antenna thereby decreasing telemetry performance. Of course, once an implantable medical device is implanted, the only way to correct the detuning, is to remove the implant, which is clearly not desired.

Thus, it is an object of the present invention to provide an implantable medical device that will ensure that fluids will not come into contact with the antenna and therefore the tuning of the antenna will remain constant.

SUMMARY OF THE INVENTION

These and other objects are achieved with an implantable medical device that includes a hermetically sealed housing that contains electronic circuitry. A feedthrough is disposed on an external surface of the housing. A wire is disposed around the external surface of the housing. The wire has one end connected to the feedthrough so that the wire is in electric communication with at least a portion of the electronic circuitry. A heat shrink tube is sealingly disposed about substantially the entire external surface of the wire to prevent fluids from contacting the antenna wire and thereby detuning the antenna wire. An antenna surround is disposed about the tube.

BRIEF DESCRIPTION OF THE DRAWINGS

The invention can be more fully understood from the following detailed description taken in conjunction with the accompanying drawings, in which:

FIG. 1 is a perspective view of an implantable infusion pump in accordance with the present invention;

FIG. 2 is a schematic cross sectional view of the implantable infusion pump in accordance with the present invention;

FIG. 3 is a perspective view of the antenna wire;

DETAILED DESCRIPTION OF THE PREFERRED EMBODIMENTS

Figure 4:
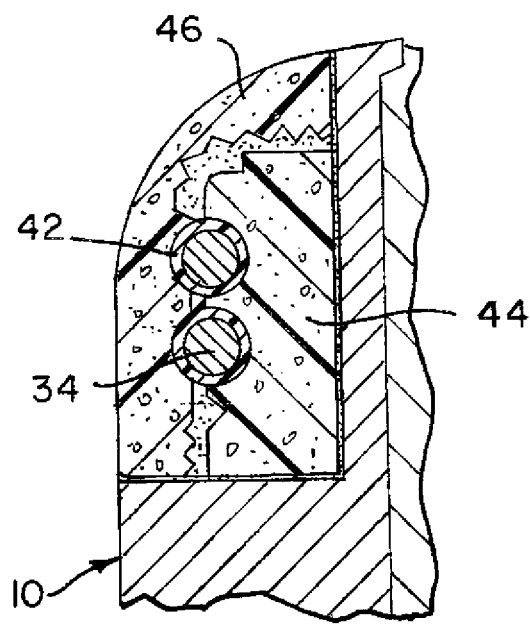
FIG. 4 is a partial cross-sectional view of the antenna wire, heat shrink tube and antenna surround assembly.

Referring now to FIGS. 1-5, an implantable medical device 10. In a currently preferred embodiment, device 10 is an implantable infusion pump. But device 10 could be a cardiac rhythm management device, an electrical stimulation device, a gastric band device or any other implantable medical device such as, for example, any implantable sensors, known to those skilled in the art.

Wireless technology ensures the transfer of data between the implanted pump 10 and an external control unit. The wireless link between the pump and the control unit is typically a radio-frequency link relying on an inductive coupling of two loop antennas, one on the external device and one on or in the implantable medical device.

Device 10, which is illustrated as an infusion pump, has a hermetically sealed housing 12 that contains electronic circuitry 14. Housing 12 is preferably made of a biocompatible material, such as titanium. The pump as shown schematically in FIG. 2 contains two separate chambers mounted on a pump base plate 16. The outer chamber 18 (the pressure chamber) contains a liquid gas mixture (preferably n-butane) used as a propellant to exert a constant force onto the titanium bellows enclosure 20 of the inner chamber 22, which is a drug reservoir. On the upper side of base plate 16 is a third chamber 24 that contains the electronics 14, a battery 26, a valve 28 and a valve actuator 30. At an outlet 32, a catheter (not shown) can be connected to deliver the drug to its application site. In order for the pump to communicate with an external control unit, an antenna 34, in the form of a wire, is disposed around the external surface of housing 12. Wire 34 is preferably made of a biocompatible metal, such as niobium. Wire 34 can be purchased from Sored SA of La Chaux-de-Fonds, Switzerland. Wire 34, in one preferred embodiment, has a diameter of 1 mm and a length of 450 mm. But, of course, other dimensions may be used depending upon, for example, the carrier frequency, the size of the implantable medical device or its intended location within the body. To obtain a hermetic electrical connection between the antenna and the pump electronics in chamber 24, a feedthrough 36 disposed on external surface 12 is used.

Referring now to FIG. 3, antenna 34 has a first end 38 and an external surface 40. Antenna wire 34 is wound around the external surface 12 of housing 10 about two times. First end 38 of antenna wire 34 is fixedly connected, preferably by laser welding to feedthrough 36 so that the wire is in electric communication with at least a portion of the electronic circuitry 14.

Figure 5:
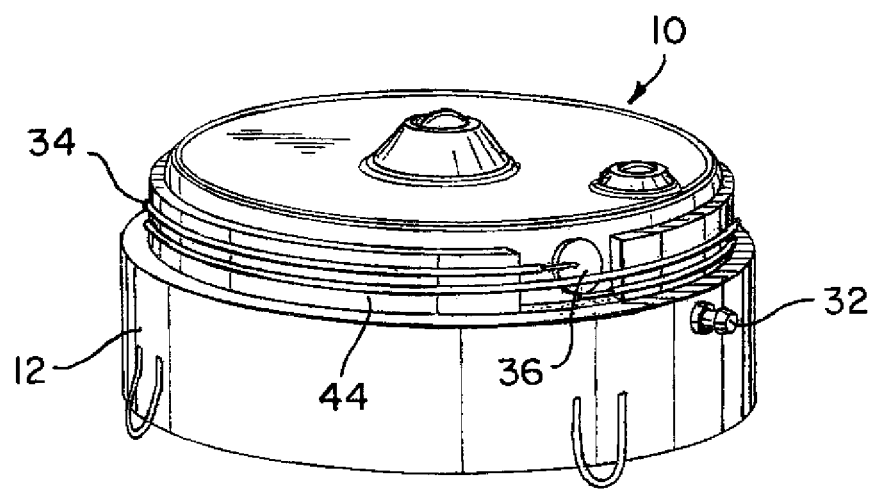
FIG. 5 is a perspective view of the implantable infusion pump with the outer antenna surround removed to show the antenna wire with the heat shrink tube wrapped around the pump housing.

Referring now to FIGS. 4 and 5, antenna wire 34 is encapsulated in a heat-shrink tube 42 to ensure that no fluids, including body fluids come into contact with wire 34, which would cause detuning of the antenna. Heat shrink tube 42 is preferably made of a biocompatible material, such as fluorinated ethylene-propylene (FEP). Heat shrink tube 42 can be purchased from Zeus of Raritan, N.J., USA. Heat shrink tube 42, in one preferred embodiment, has a diameter of 1.14 mm before shrinkage and a maximum internal diameter of 0.991 mm after shrinkage, and a length of 450 mm. But, of course, just like wire 34, heat shrink tube can have other dimensions depending upon, for example, the carrier frequency, the size of the implantable medical device or its intended location within the body.

As illustrated in FIG. 5, heat shrink tube 42 is preferably disposed about substantially the entire external surface of antenna wire 34. Heat shrink tube 42 is placed about wire 34 and sealed in place in an oven for two to fifteen minutes at about 200° C. During this heat shrinking process, the distal ends of antenna wire 34 may remain exposed, as illustrated in FIG. 5. Antenna wire 34 is preferably wound two times around the external surface of housing 10. An antenna inner surround 44 and an antenna outer surround 46 are disposed about heat shrink tube 42. Referring now to FIG. 4, inner surround 44 is preferably glued to the exterior surface of housing 10. The glue is preferably an epoxy glue, such as Loctite Hysol M31-CL. The antenna wire 34 with the heat shrink tube already shrunk thereon, is then placed about inner surround 44. As discussed above, end 38 of antenna wire 34 is then laser welded to feedthrough 36. To eliminate the exposure of the distal ends of antenna wire 34, each distal end as well as the entire exposed portion of the feedthrough 36 is subject to a potting (or caulking) by applying a glue entirely around these surfaces. In a currently preferred embodiment, the glue is Nusilmed 1137, which is commercially available from Nusil Technology Co. of Carpinteria, Calif., USA. Thus, the entire antenna wire and feedthrough, due to the heat shrink tube and the potting glue, are now completely sealed from exposure to any external fluids, including body fluids. Since fluids are prevented from contacting the antenna wire, the implantable device antenna will not become detuned during use. Outer surround 46 is then glued to the inner surround 44 with the epoxy glue, preferably Loctite Hysol M31-CL.

It will be understood that the foregoing is only illustrative of the principles of the invention, and that various modifications can be made by those skilled in the art without departing from the true spirit and scope of the invention as defined by the appended claims. Other arrangements can similarly be assembled without departing from the invention.

What is claimed is:

1. An implantable medical device comprising:
   a hermetically sealed housing containing electronic circuitry;
   a feedthrough disposed on an external surface of said housing;
   an antenna wire having a first distal end, a second distal end and an external surface, said antenna wire being disposed around said external surface of said housing, said antenna wire having said one end connected to said feedthrough so that said antenna wire is in electric communication with at least a portion of said electronic circuitry;
   a tube having a hollow cylindrical shape being sealingly disposed about substantially said entire external surface of said antenna wire to prevent fluids from contacting the wire and thereby detuning the antenna wire; and
   an antenna surround disposed about said tube.

2. The device according to claim 1, wherein said housing is made of a biocompatible material.

3. The device according to claim 2, wherein said housing is made of metal.

4. The device according to claim 1, wherein said antenna wire is made of metal.

5. The device according to claim 4, wherein said antenna wire is made of niobium.

6. The device according to claim 5, wherein said first distal end of said antenna wire is welded to said feedthrough.

7. The device according to claim 6, wherein said weld is a laser weld.

8. The device according to claim 1, wherein said tube is a heat shrink tube.

9. The device according to claim 8, wherein said tube is made of a biocompatible material.

10. The device according to claim 9, wherein said tube is made of fluorinated ethylene-propylene.

11. The device according to claim 1, wherein said antenna wire is wound around said housing for at least two windings.

12. The device according to claim 1, wherein said antenna surround is comprised of an inner antenna surround and an outer antenna surround.

13. The device according to claim 1, further comprising a glue being disposed on each distal end of said antenna wire as well as the entire exposed portion of said feedthrough.

14. A method of maintaining the tuning of an antenna in an implantable medical device constant, said method comprising the steps of:
   manipulating a hermetically sealed housing containing electronic circuitry and a feedthrough disposed on an external surface of said housing, said feedthrough having an exposed external surface;
   manipulating an antenna wire having a first distal end, a second distal end and an external surface;
   placing said antenna wire around said external surface of said housing;
   connecting said first distal end of said antenna wire to said feedthrough so that said antenna wire is in electric communication with at least a portion of said electronic circuitry;
   sealingly placing a tube having a hollow cylindrical shape about substantially said entire external surface of said antenna wire to prevent fluids from contacting the wire and thereby detuning the antenna wire; and
   placing an antenna surround about said tube.

15. The method according to claim 14, further comprising the step of:
   potting a glue on each distal end of said antenna wire as well as the entire exposed portion of said feedthrough such that the entire antenna wire and feedthrough, due to the tube and the potting glue, are completely sealed from exposure to any external fluids.

16. The method according to claim 15, wherein the tube is a heat shrink tube.

* * * * *